(12) United States Patent
Xu et al.

(10) Patent No.: US 9,133,045 B2
(45) Date of Patent: Sep. 15, 2015

(54) METHODS AND WATER TREATMENT SYSTEMS FOR REDUCING BISPHENOL A RELEASE

(75) Inventors: Yanjie Xu, Longmont, CO (US); Robert Cabrera, Longmont, CO (US)

(73) Assignee: EMPIRE TECHNOLOGY DEVELOPMENT LLC, Wilmington, DE (US)

( * ) Notice: Subject to any disclaimer, the term of this patent is extended or adjusted under 35 U.S.C. 154(b) by 105 days.

(21) Appl. No.: 13/978,239

(22) PCT Filed: Jul. 11, 2012

(86) PCT No.: PCT/US2012/046250
§ 371 (c)(1),
(2), (4) Date: Jul. 3, 2013

(87) PCT Pub. No.: WO2013/009867
PCT Pub. Date: Jan. 17, 2013

(65) Prior Publication Data
US 2014/0197100 A1 Jul. 17, 2014

(51) Int. Cl.
*C02F 3/34* (2006.01)
*C08K 5/544* (2006.01)
*C12N 11/08* (2006.01)

(52) U.S. Cl.
CPC ............... *C02F 3/342* (2013.01); *C08K 5/544* (2013.01); *C12N 11/08* (2013.01); *C08K 2201/019* (2013.01)

(58) Field of Classification Search
USPC .......................................................... 210/606
See application file for complete search history.

(56) References Cited

U.S. PATENT DOCUMENTS

| | | | |
|---|---|---|---|
| 3,625,827 A | 12/1971 | Wildi et al. | |
| 3,678,079 A | 7/1972 | Carty et al. | |
| 4,006,271 A | 2/1977 | French et al. | |
| 4,889,876 A | 12/1989 | Yamamoto | |
| 4,923,599 A | 5/1990 | Bowers | |
| 4,975,203 A | 12/1990 | Cook et al. | |
| 5,475,138 A | 12/1995 | Pal et al. | |
| 7,358,290 B2 | 4/2008 | Wenz et al. | |
| 7,799,191 B2 | 9/2010 | Yu et al. | |
| 7,872,068 B2 | 1/2011 | Khosravi et al. | |
| 2010/0184121 A1* | 7/2010 | Misiak et al. | 435/29 |
| 2010/0210745 A1 | 8/2010 | McDaniel et al. | |
| 2012/0164699 A1 | 6/2012 | Anderson | |

OTHER PUBLICATIONS

Acevedo, et al., "Degradation of polycyclic aromatic hydrocarbons by free and nanoclay-immobilized manganese peroxidase from Anthroacolphyllum discolor", Chemosphere, (2010), pp. 271-278, vol. 80, No. 3, Elsevier.

Bawa, et al., "Enzymatic Reduction of Ketones to Optically Active Secondary Alcohols", Journal of Physical Science, (2008), pp. 1-5, vol. 19, No. 2, Penerbit Universiti Sains Malaysia.

Gallucci, "Polycarbonate Hydrolysis," http://kbam.geampod.com/KBAM/reflection/assets/19514.pdf, NPE, cited in 2010, 5 pages.

Glad, et al., "Use of silane monomers for molecular imprinting and enzyme entrapment in polysiloxane-coated porous silica", Journal of Chromatography A, (1985), pp. 11-23, vol. 347, Elsevier.

Grady, et al. "Polymerization of styrene-isoprene on glass cloth for use in composite manufacture", Polymer Composites, (1998), pp. 579-587, vol. 19, No. 5, Wiley InterScience.

Graham, et al., "Identification and characterization of a multidomain hyperthermophilic cellulase from an archaeal enrichment", Nature Communications, (Jul. 5, 2011), vol. 2, Article No. 375, Nature Publishing Group.

Heider, et al., "Purification, characterization, and metabolic function of tungsten-containing aldehyde ferredoxin oxidoreductase from the hyperthermophilic and proteolytic archaeon Thermococcus strain ES-1", Journal of Bacteriology, (1995), pp. 4757-4764, vol. 177, No. 6, American Society for Microbiology.

Hwang et al., "Scratch Resistant and Transparent UV-Protective Coating on Polycarbonate," Journal of Sol-Gel Science and Technology, (2003), pp. 783-787, vol. 26, No. 1-3, Springer.

Jiang, et al., "Occurrence and transform of emerging micropollutants in the environment, analytical challenges and treatment technologies: A global case study", Proceedings of the 12th International Conference on Environmental Science and Technology (CEST2011). Rhodes, Greece, Sep. 2011, pp. B442-434, entire document.

Kim, et al., "Synthesis and characterization of nanoporous silica support for enzyme immobilization", Colloids and Surfaces A: Physicochemical and Engineering Aspects, (2004), pp. 113-117, vol. 241, No. 1-3, Elsevier.

McQuade, et al., "Conjugated Polymer-Based Chemical Sensors", Chemical Reviews, (2000), pp. 2537-2574, vol. 100, No. 7, American Chemical Society.

Mercea, "Physiochemical Processes Involved in Migration of Bisphenol A from Polycarbonate", Journal of Applied Polymer Science, (2009), pp. 579-593, vol. 112, No. 2, Wiley InterScience.

Mitsunaga, et al., "Intercalated Polycarbonate/Clay Nanocomposites: Nanostructure Control and Foam Processing", Macromolecular Materials and Engineering, (2003), pp. 543-548, vol. 288, No. 7, Wiley VCH Verlag.

Nam, et al., "Foam processing and cellular structure of polypropylene/clay nanocomposites", Polymer Engineering and Science, (2002), pp. 1907-1918, vol. 42, No. 9, Wiley.

Pasumansky, et al., "Lithium Aminoborohydrides: Powerful, Selective, Air-Stable Reducing Agents", Organic Process Research & Development, (2006), pp. 959-970, vol. 10, No. 5, American Chemical Society.

PCT International Search Report and Written Opinion dated Oct. 3, 2012 in related PCT Patent Application Serial No. PCT/US2012/046250, 11 pages.

(Continued)

*Primary Examiner* — Chester Barry
(74) *Attorney, Agent, or Firm* — Foley & Lardner LLP

(57) ABSTRACT

Disclosed are methods, compositions and systems pertaining to polymer coatings that entrap enzymes, specifically enzymes capable of reducing carboxylic acids.

20 Claims, 1 Drawing Sheet

(56) References Cited

OTHER PUBLICATIONS

Pekala, et al., "Alcohol Dehydrogenases as Tools for the Preparation of Enantiopure Metabolites of Drugs with Methyl Alkyl Ketone Moiety", Scientia Pharmaceutica, (2009), pp. 9-17, vol. 77, No. 1, Österreichischer Apothekerverlag.

Suzuki, et al., "Environmental Fate of Bisphenol A and Its Biological Metabolites in River Water and Their Xeno-estrogenic Actvity," Environmental Science and Technology, (2004), pp. 2389-2396, vol. 38, No. 8, American Chemical Society.

Wang, et al., "Preparation of Highly Exfoliated Epoxy/Clay Nanocomposites by "Slurry Compounding": Process and Mechanisms", Langmuir, (2005), pp. 3613-3618, vol. 21, No. 8, American Chemical Society.

White, et al., "Carboxylic acid reductase: a new tungsten enzyme catalyses the reduction of non-activated carboxylic acids to aldehydes", European Journal of Biochemistry, (1989) pp. 89-96, vol. 184, No. 1, Wiley InterScience.

Xu, Dingying, Durability and Xu, "Durability and Adhesion of a Model Epoxy Adhesive Bonded to Modified Silicon Substrates", Doctorate Thesis, (Jun. 10, 2004), p. 1-170, Virginia Polytechnic Institute and State University.

* cited by examiner

METHODS AND WATER TREATMENT SYSTEMS FOR REDUCING BISPHENOL A RELEASE

CROSS-REFERENCE TO RELATED APPLICATIONS

This application is a U.S. National Stage filing under 35 U.S.C. §371 of International Application Serial No. PCT/US2012/046250, filed on Jul. 11, 2012, the entire disclosure of which is hereby incorporated by reference for all purposes in its entirety as if fully set forth herein.

TECHNICAL FIELD

This disclosure relates generally to methods and compositions pertaining to chemical and enzymatic treatment of plastics and polymers. In certain embodiments, the disclosure relates to reducing carboxylic acids in plastics and polymers.

BACKGROUND

The following description is provided to assist the understanding of the reader. None of the information provided or references cited is admitted to be prior art.

Bisphenol A (BPA) is an organic molecule containing two phenol groups and two methyl groups attached to a central carbon ($HOC_6H_4$—$C(CH_3)_2C_6H_4OH$; $C_{15}H_{16}O_2$). BPA is the primary monomer component of polycarbonate and polyester carbonate plastic as well as epoxy resins. BPA-based plastics and resins are used in many different consumer plastic products, including use of epoxy resin as a protective lining for metal food and beverage cans, hard plastic bottles, food storage containers, stretchable PVC films, and other products. Over 8 billion pounds of BPA is produced each year and BPA has been found in human blood and urine in more than 80 biomonitoring studies.

BPA monomers can be released from epoxy resin and polycarbonates when polymerization is incomplete; in addition leaching of BPA increases under high heat and acidic conditions. BPA is known to bind estrogen receptors and has been shown to have effects in rodents exposed to levels of BPA similar to those seen in humans. BPA exposure in humans has been suggested to contribute to several disorders, including diabetes, obesity, prostate and breast cancer, as well as infertility and genital tract abnormalities.

SUMMARY

The compositions and methods described herein relate to chemical and enzymatic treatment of plastics and polymers and involve the entrapment of enzymes in polymers.

In one aspect, the present technology provides compositions including at least one carboxylic acid-reducing enzyme and a polymer, wherein the polymer comprises organic silane.

In another aspect, the present technology provides methods of treating a composition comprising a bisphenol A (BPA) precursor. In some embodiments, the methods include contacting the composition comprising the BPA precursor with a carboxylic acid-reducing composition, wherein the carboxylic acid-reducing composition includes a carboxylic acid-reducing enzyme and organic silane, and wherein the BPA precursor includes a polymer that produces BPA monomers upon polymer hydrolysis.

In yet another aspect, the present technology provides methods of treating water that contains 2,2-bis(4-hydroxyphenyl)propanoic acid (BPA-COOH). In some embodiments, the methods include contacting the water with (a) at least one carboxylic acid-reducing enzyme entrapped in a polymer, and (b) at least one carbonyl-reducing compound under conditions wherein the BPA-COOH is degraded.

In still another aspect, the present technology provides water treatment systems that contain 2,2-bis(4-hydroxyphenyl)propanoic acid (BPA-COOH). In some embodiments, the water treatment systems include (a) an inlet to a treatment area, wherein the treatment area holds (i) a carboxylic acid-reducing composition comprising at least one carboxylic acid-reducing enzyme entrapped in polymerized organic silane, and (ii) at least one carbonyl-reducing compound; and (b) an outlet from the treatment area.

In some illustrative embodiments of the compositions and methods described herein, the carboxylic acid-reducing enzyme is entrapped in the polymer. In some illustrative embodiments, the polymer is organic silane. In some embodiments, the organic silane is formed from polymerization of methyltrimethoxysilane and gamma-aminopropyltriethoxysilane. In some embodiments, at least one carboxylic acid-reducing enzyme comprises one or more of carboxylate reductase, aldehyde ferredoxin oxidoreductase, formaldehyde ferredoxin oxidoreductase, glyceraldehyde-3-phosphate ferredoxin oxidoreductase, and (2R)-hydroxycarboxylate-viologen-oxidoreductase.

In some embodiments of the compositions and methods provided herein, the composition is in the form of a non-perforated sheet, a perforated sheet, beads, dry particulate, or gel. In some embodiments, the carboxylic acid-reducing enzyme entrapped in the polymer is in the form of a gel suspended in an adhesive film.

In some embodiments of the compositions and methods of the present technology, the BPA precursor comprises polycarbonate, polyester carbonate, or an epoxy resin. In some embodiments, the carboxylic acid-reducing composition is contacted with at least a portion of the composition comprising the BPA precursor. In some embodiments, contacting includes polymerizing the carboxylic acid-reducing composition directly onto at least a portion of the composition comprising the BPA precursor.

In some embodiments of the water treatment systems of the present technology, the carbonyl-reducing composition is one or more of sodium borohydride, lithium aminoborohydride, and alcohol dehydrogenase. In some embodiments, the carboxylic acid reductase and the carbonyl-reducing composition are contacted with the water sequentially. In some embodiments, the treatment area further comprises a first chamber that holds the carboxylic acid-reducing composition and a second chamber that holds the carbonyl-reducing composition.

The foregoing summary is illustrative only and is not intended to be in any way limiting. In addition to the illustrative aspects, embodiments and features described above, further aspects, embodiments and features will become apparent by reference to the following drawings and the detailed description.

DETAILED DESCRIPTION

Figure 1A:
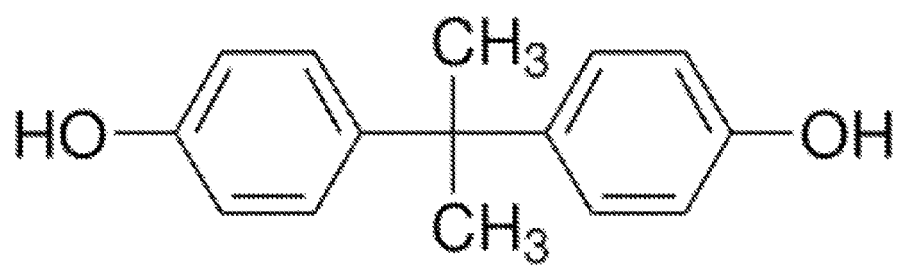
FIG. 1A is a schematic diagram of the monomer bisphenol A (BPA).

In the following detailed description, reference is made to the accompanying drawings, which form a part hereof. In the drawings, similar symbols typically identify similar components, unless context dictates otherwise. The illustrative embodiments described in the detailed description, drawings, and claims are not meant to be limiting. Other embodiments may be utilized, and other changes may be made, without departing from the spirit or scope of the subject matter presented here.

The technology is described herein using several definitions, as set forth throughout the specification.

Unless otherwise stated, the singular forms "a," "an," and "the" as used herein include plural reference.

As used herein, "BPA precursor" refers to a polymer that can be hydrolyzed to release the monomer bisphenol A (BPA). BPA precursors include, but are not limited to, e.g. plastics and resins created using BPA monomers. Such polymers are used in many different consumer plastic products, including, but not limited to, e.g. protective linings for metal food and beverage cans, hard plastic bottles, food storage containers, stretchable PVC films, eye glass lenses and goggle, windows, CDs and DVDs, and other products.

As used herein, "entrapping" or "entrapment" refers to a molecule immobilized within the interstitial spaces of a porous substance, such as a polymer, and that cannot easily be removed from the substance by washing or rinsing with a liquid. The entrapped molecule may not necessarily be covalently bound to the substance.

As used herein, "carboxylic acid-reducing composition" refers to a composition that reduces carboxylic acids. The composition may include a carboxylic-acid reducing enzyme.

As used herein, "carboxylic acid-reducing enzyme" refers to an enzyme that is catalyzes a reaction in which carboxylic acid is reduced. Oxidoreductases are generally classified under EC numbers 1.1-1.21 and 1.97, and are found in bacteria, plants, and animals. Many oxidoreductases capable of reducing a carboxylic acid group are classified under EC number 1.2 and act on aldehyde or oxo groups, or are alcohol oxidoreductases classified under EC number 1.1. Examples of carboxylic acid-reducing enzymes include, without limitation: carboxylate reductase, aldehyde dehydrogenase (NAD+), aldehyde dehydrogenase (NADP+), aldehyde dehydrogenase [NAD(P)+], aldehyde dehydrogenase (FAD-independent).

As used herein, "carbonyl-reducing composition" refers to an enzyme or a chemical compound that can reduce a carbonyl group, such as a ketone group, to an alcohol. Exemplary carbonyl-reducing compositions include sodium borohydride, lithium aminoborohydride, and alcohol dehydrogenase from *Pyrococcus furiosus* (1.1.1.2) or yeast.

As used herein, the term "about" in quantitative terms refers to plus or minus 10%. For example, "about 3%" would encompass 2.7-3.3% and "about 10%" would encompass 9-11%. Moreover, where "about" is used herein in conjunction with a quantitative term it is understood that in addition to the value plus or minus 10%, the exact value of the quantitative term is also contemplated and described. For example, the term "about 3%" expressly contemplates, describes and includes exactly 3%.

A. Bisphenol A (BPA) and BPA Polymers

Figure 1B:
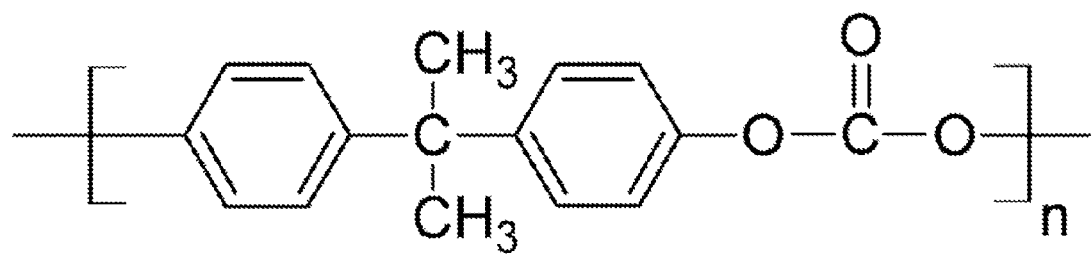
FIG. 1B is a schematic diagram of a single unit of polycarbonate.

Bisphenol A (BPA) is the monomer component of polycarbonate, polyester carbonate, and epoxy resins. The chemical structure of BPA is shown in FIG. 1A. In polycarbonate, BPA monomers are linked via a carbonate linkage. FIG. 1B shows a schematic diagram of the chemical structure of polycarbonate. When a BPA-based polymer is hydrolyzed, it releases components of the polymer, including the BPA monomer. Thus, a polymer that is created using BPA monomers and can release the BPA monomers upon hydrolysis is referred to herein as a BPA precursor.

A common pathway involved in the hydrolysis of polycarbonate and other BPA-based polymers is acid catalysis. While acid catalysis can occur from exposing a BPA-based polymer to an acid, there are also carboxylic acid sources in BPA-based polymers themselves. For example, carboxylic acid ester mould release agents are sometimes left over from the production of polycarbonate products (around 0.1-0.5 weight percent of polycarbonate). Carboxylic acids can also be found when polyester carbonate copolymer is used in making a polycarbonate. If the polyester linkage is hydrolyzed (by water, for example), a carboxylic acid is formed. Therefore, addition of acid scavengers can improve the hydrolysis resistance of BPA-based polymers.

B. Compositions to Prevent or Reduce BPA Hydrolysis

Disclosed herein are compositions and methods for preventing or reducing BPA hydrolysis in BPA-containing compounds. In some embodiments, the compositions include an acid reducing enzyme, such as a carboxylic acid reducing enzyme, entrapped in a polymer matrix.

1. Carboxylic Acid-Reducing Enzymes of the Present Technology

Several enzymes are known to reduce carboxylic acid groups. Oxidoreductases are generally classified under EC numbers 1.1-1.21 and 1.97 and are found in bacteria, plants, and animals. Many oxidoreductases capable of reducing a carboxylic acid group are classified under EC number 1.2 and act on aldehyde or oxo groups, or are alcohol oxidoreductases classified under EC number 1.1. Exemplary carboxylic acid-reducing enzyme classes include: carboxylate reductase (EC No. 1.2.99.6), aldehyde ferredoxin oxidoreductase (EC No. 1.2.7.5), aldehyde dehydrogenase (FAD-independent) (EC No. 1.2.99.7), aldehyde dehydrogenase (NAD+) (EC No. 1.2.1.3), aldehyde dehydrogenase (NADP+) (EC No. 1.2.1.4), aldehyde dehydrogenase [NAD(P)+] (EC No. 1.2.1.5), and (2R)-hydroxycarboxylate-viologen-oxidoreductase (EC No. 1.1.99.30).

Carboxylate reductase is a type of enzyme found in bacteria that requires a metal ion, such as tungsten, iron, magnesium, or zinc. The enzyme is also known by other names, such as carboxylic acid reductase (CAR), aldehyde oxidoreductase (AOR), aldehyde ferredoxin oxidoreductase, aldehyde reductase, formaldehyde ferredoxin oxidoreductase, glyceraldehyde-3-phosphate ferredoxin oxidoreductase, and hydroxycarboxylate viologen oxidoreductase, NAD(P)-dependent carboxylic acid reductase (GriC), and ATP-dependent carboxylic acid reductase (GriD).

Enzymes useful in the disclosed compositions can be isolated from natural sources (e.g., from bacteria, plants, yeast and animals), can be produced by recombinant methods known in the art, and/or can be purchased from commercial vendors.

2. Polymers and Enzyme Entrapment

Enzymes entrapped in silane monomers retain their catalytic properties and significant levels of enzymatic activity. Studies have shown that the siloxane polymer produced from mixing bis(2-hydroxyethyl)aminopropyltriethoxysilane and tetraethoxysilane can be used to entrap a variety of enzymes, including glucose oxidase, trypsin, alkaline phosphatase, and horseradish peroxidase (see e.g., Glad et al., *J Chromatography* 1985; 347:11-23). Depending on whether the siloxane polymer used to entrap glucose oxidase was mixed with or without silica particles, the glucose oxidase showed activity yields between 5% and 40%. Glucose oxidase and horseradish peroxidase was also co-entrapped in polysiloxane polymer and the resulting activity yields for both enzymes showed that the enzymes were not destroyed.

Accordingly, organic silane polymers can be used to entrap enzymes and form, for example, highly abrasion resistant coatings for polycarbonate surfaces. For example, the siloxane hydrolyzed C1-C2 alkyltri(lower alkoxy) silane coatings can be formed on polycarbonate surfaces, by combining methyltrimethoxysilane and gamma-aminopropyltriethoxysilane. Another example of a organic silane polymer that can be used to entrap enzymes and coat a polycarbonate is a siloxane formed from methoxytrimethylsilane and dimethyldimethoxysilane in combination with titanium oxide (Hwang et al., *J. Sol-Gel Sci. Tech.* 2003, 26: 783-787). The combination of bis(2-hydroxyethyl)aminopropyltriethoxysilane and tetraethoxysilane can also used to form a polymer that entraps enzymes.

Other polymers that may be used to entrap enzymes include styrene-isoprene polymers (Polymer Composites. Oct 1998. 19 (5), pp 579-587).

Enzyme co-factors can also be covalently linked to the organic silane polymer before entrapping enzymes in the polymer. For example, NAD(P) or ATP can be covalently linked to any of the components of the organic silane before polymerizing and entrapping a carboxylic acid reductase such as GriC or GriD. In addition, multiple enzymes and co-factor molecules can be entrapped using this technology. For example, both GriC and GriD, as well as their co-factors NAD(P) and ATP could all be co-entrapped in organic silane.

3. Polymer/Enzyme Compositions

The polymer/enzyme compositions disclosed herein can be produced in a number of forms (e.g., solid, powder, gel, adhesive). For example, silane polymers that contain entrapped enzymes can also be broken up into particulates which are then combined with other polymers. For example, Hwang et al. describes making a polymer by mixing a sol of nanoparticles of titanium oxide with a sol of methoxytrimethylsilane and dimethyldimethoxysilane. *J. Sol-Gel Sci. Tech* 2003, 26: 783-787. An organic silane polymer in particulate or nanoparticle form containing entrapped enzyme could be combined with the polymer and titanium oxide sols to form a composite material with enzymatic activity. An enzyme-particulate can be formulated as a sol and then mixed with other polymers, including organic silanes, to form a composite material that is resistant to wearing, scratching, and ultraviolet (UV) radiation damage.

Additionally or alternatively, polymerized organic silanes can also be ground into particles used as a sol-gel powder for incorporation into other polymer coatings. In another instance the particles can be nanoclay or nanoclay composites (Polym. Eng. Sci., 42(9): 1907, Macromol. Mater. Eng., 288: 543). The silicate nanoclay can have enzyme absorbed to the surface or the surface can be silanized, epoxy coated, or epoxy silane coated (Chemosphere. 2010 Jun; 80(3):271-8, Langmuir. 2005 Apr 12; 21(8):3613-8) for covalent bond formation with the enzyme.

Methods for creating clear, abrasion-resistant coatings on a polycarbonate substrate have also been described. U.S. Pat. No. 4,006,271 describes creating an organic silane mixture using a hydrolyzed C1-C2 alkyltri(lower alkoxy) silane to coat polycarbonate and create a layer that is highly abrasion resistant. Hwang et al. (*J. Sol-Gel Sci. Tech.*, 2003, 26:783-787) have also shown that $TiO_2$ nanoparticles modified with 3-glycidoxypropyl-trimethoxysilane (GPTMS) and $SiO_2$ modified with acetyl acetone, mixed with methoxytrimethylsilane and dimethyldimethoxysilane can form a highly scratch-resistant and ultraviolet light-protective coating for polycarbonate.

A BPA precursor, e.g. polycarbonate, that is coated with the polymer/enzyme may be in a variety of forms. For example, the coated BPA precursor may be in the form of beads, sheets, perforated sheets, rods, cylinders, spheres, cones, prisms, pyramids, cubes, or other polyhedric or ellipsoid shapes. The coated BPA precursor composition may also be porous. Additionally or alternatively, a substrate other than a BPA precursor can include the polymer/enzyme composition. Such substrates can be in the form of beads, sheets, perforated sheets, rods, cylinders, spheres, cones, prisms, pyramids, cubes, or other polyhedric or ellipsoid shapes. The coated substrate composition may also be porous. Such coated substrates may then be positioned in contact with a PBA precursor, such that the polymer/enzyme composition contacts the PBA precursor.

C. Methods to Prevent or Reduce BPA Hydrolysis

BPA precursor compositions can be treated with an organic silane/carboxylic acid-reducing enzyme composition. A plethora of products that can be treated using the compositions and methods described herein, including, without limitation, water bottles, eye glass lenses, goggle lenses, interiors of food and beverage containers, medical devices, stretchable PVC films, eye glass lenses and goggle lenses, windows, CDs and DVDs, and other products.

Treating a BPA precursor composition with an enzyme/polymer composition means contacting or coating the entire surface or part of the surface of the BPA precursor. If the BPA precursor composition is perforated or porous, an organic silane/carboxylic acid-reducing enzyme composition may be applied as a coating on the inner surface of the BPA precursor composition as well. Methods of applying organic silane/carboxylic acid-reducing enzyme coating to a BPA precursor composition may include spraying, brushing, vapor deposition, or dipping.

D. Water Purification Using Carboxylic Acid-Reducing Enzymes

River water has been shown to contain modified BPA molecules that are by-products of metabolism by mammals and bacteria, including BPA-COOH (2,2-bis(4-hydroxyphenyl) propanoic acid) (Suzuki et al., Environ. Sci. Technol. 2004, 38, 2389-2396). BPA-COOH can bind the estrogen receptor and significantly increases the proliferation of MCF-7 cells in culture compared to controls at concentrations of $10^{-5}$ to $10^{-4}$ M (p<0.05), an indication of estrogenic activity. In contrast, the compound BPA-OH (2,2-bis(4-hydroxyphenyl)-1-propanol) does not significantly increase MCF-7 cell proliferation above controls at the same concentrations.

Enzymes that can reduce carboxylic acids can be entrapped in polymers as described herein and used to convert BPA-COOH to the less estrogenic compound BPA-OH. A carboxylic acid-reducing enzyme, e.g. carboxylate reductase, can use BPA-COOH as a substrate and reduce the carboxylic acid group to an aldehyde. This aldehyde-containing compound can then be treated with a second reducing agent, such as sodium borohydride, lithium aminoborohydride, or an enzyme (e.g. an alcohol dehydrogenase from *Pyrococcus furiosus* or yeast; Bawa et al., *J. Phys. Sci.*, Vol. 19(2), 1-5, 2008; Pekala et al., *Sci Pharm*. 2009; 77: 9-17) to convert the ketone to a hydroxyl group, resulting in BPA-OH.

Using the technology provided herein, a purification system for water that may contain BPA-COOH can be made. In some embodiments of the system, the water moves through a first chamber that contains a carboxylic acid-reducing enzyme, e.g. carboxylate reductase, entrapped in a polymer, e.g. an organic silane. In this chamber, the carboxylate group of BPA-COOH is reduced. The polymer/enzyme composition can be formed into beads, rods, perforated sheets, or other forms, or coated on beads, rods, perforated sheets, or other forms made of another polymer. The polymer/enzyme composition is situated to allow the water to be treated to flow over the interior surface (or exterior surface if the composition is permeable) of the composition. The water being purified then flows to a second chamber, in which the water is exposed to a ketone-reducing agent, such as sodium borohydride, lithium aminoborohydride, or an enzyme (e.g. alcohol dehydrogenase). Use of sodium borohydride in water purification is known in the art, such as in U.S. Pat. Nos. 4,975,203 and 4,923,599. Lithium aminoborohydrides have recently been shown to be able to reduce alkyl methanesulfonate esters in aqueous solution (*Org. Process Res. Dev.*, 2006, 10 (5), pp 959-970).

Enzymes used to convert the ketone to an alcohol include alcohol dehydrogenases (EC No. 1.1). Exemplary enzymes may include, for example, alcohol dehydrogenase from *Pyrococcus furiosus* (EC No. 1.1.1.2) or yeast (Pekala et al., *Sci Pharm.* 2009; 77: 9-17). Such enzymes may be entrapped in an organic silane as disclosed herein. As described above, the entrapped enzyme may be coated on an unperforated sheet, a perforated sheet, or beads.

EXAMPLES

The present compositions, methods and systems, thus generally described, will be understood more readily by reference to the following examples, which are provided by way of illustration and are not intended to be limiting of the present methods and systems. The following is a description of the materials and experimental procedures used in the Examples.

Example 1

Entrapping Carboxylate Reductase in an Organic Silane

Purified methyltrimethoxysilane and gamma-aminopropyltriethoxysilane are each partially hydrolyzed by treating with 0.01 N hydrochloric acid for 3 hours. A portion (15 ml) of the hydrolyzed methoxysilane is then mixed (while agitating) with purified carboxylate reductase, 0.25 ml of acetic acid, 2.0 ml ethyleneglycol monohexylether, and 2.5 ml of the partially hydrolyzed gamma-aminopropyltriethoxysilane. The combined solution is coated onto a polycarbonate surface that is cleaned with isopropyl alcohol. The coated polycarbonate is dried for 30 minutes, then transferred to a 50° C. drying oven for 30 minutes. The polycarbonate surface is then transferred to a curing oven maintained at 100° C. for 30 minutes. Thermophilic bacteria containing carboxylate reductase are reported to be stable at temperatures around 90° C. (Heider et al., J Bacteriol. 1995 Aug; 177(16):4757-64), and enzymes from thermophiles can have an optimal working temperature up to 109° C. (Nat Commun. 2011 Jul 5; 2:375). Curing temperature can be commensurate with enzyme's requirements for activity (e.g. ≤100° C.-109° C.). As indicated for coating with a polycarbonate, a lower temperature cured coating (e.g. 100° C. at 30 minutes) can be advantageous, depending on the enzyme used, to ensure enzyme stability.

Example 2

Action of Carboxylate Reductase on Carbonate Esters in Polycarbonate

An organic silane layer coated on a polycarbonate surface and containing entrapped carboxylate reductase is created using the method of Example 1. When a carboxylic acid is in the vicinity of an entrapped carboxylate reductase enzyme, the carboxylate reductase catalyzes a reaction in which the carboxylate group is reduced to an aldehyde group with the release of a water molecule.

Example 3

Forming a Carboxylate Reductase Enzyme-Particulate-Polymer Composite

An organic silane polymer containing entrapped carboxylate reductase is created using the process described in Example 1, without coating the organic silane polymer on polycarbonate, and then curing it. The resulting silane polymer containing entrapped enzymes is then mechanically broken into small particles. These particles may be chosen to have a maximal size to yield a maximal enzyme activity when integrated into an enzyme-particulate-polymer composite material. The enzyme-particulate is then prepared as a sol and mixed with a sol of titanium oxide nanoparticles and sols of methoxytrimethylsilane and dimethyldimethoxysilane and treated as described in Hwang et al. *J. Sol-Gel Sci. Tech.*, 26: 783-787. The resulting composite will have enzymatic activity and increased wear, scratch, and ultraviolet (UV) radiation resistance.

Example 4

Water Purification

An organic silane polymer containing entrapped carboxylate reductase is created on the surface of polystyrene beads, using the process described in Example 1. The coated beads are about 1 mm in diameter. The beads are packed into a first chamber having an inlet and a first outlet to allow continuous flow of wastewater through the chamber. The outlet of the first chamber connects to a second chamber that contains a solution of sodium borohydride (also known as sodium tetrahydridoborate).

The wastewater flows into the first chamber via the inlet and contacts the coated beads. The hydroxyl group of any BPA-COOH in the wastewater is converted to an aldehyde. The wastewater containing the BPA-aldehyde then flows into the second chamber and is allowed to react with the sodium borohydride, which converts the aldehyde to an alcohol (BPA-OH). The wastewater is then moved to a filtering chamber to remove the reaction product resulting from the reaction of the sodium borohydride.

\* \* \*

The embodiments, illustratively described herein, may suitably be practiced in the absence of any element or elements, limitation or limitations, not specifically disclosed herein. Thus, for example, the terms "comprising," "including," "containing," etc., shall be read expansively and without limitation. Additionally, the terms and expressions employed herein have been used as terms of description and not of limitation, and there is no intention in the use of such terms and expressions of excluding any equivalents of the features shown and described or portions thereof, but it is recognized that various modifications are possible within the scope of the claimed technology. Additionally, the phrase "consisting essentially of" will be understood to include those elements specifically recited and those additional elements that do not materially affect the basic and novel characteristics of the claimed technology. The phrase "consisting of" excludes any element not specified.

The present disclosure is not to be limited in terms of the particular embodiments described in this application, which are intended as illustrations of various aspects. Many modifications and variations can be made without departing from its spirit and scope, as will be apparent to those skilled in the art. Functionally equivalent compositions, apparatuses, and methods within the scope of the disclosure, in addition to those enumerated herein, will be apparent to those skilled in the art from the foregoing descriptions. Such modifications and variations are intended to fall within the scope of the appended claims. The present disclosure is to be limited only by the terms of the appended claims, along with the full scope of equivalents to which such claims are entitled. It is to be understood that this disclosure is not limited to particular methods, reagents, compounds, compositions or biological systems, which can, of course, vary. It is also to be understood that the terminology used herein is for the purpose of describing particular embodiments only, and is not intended to be limiting.

In addition, where features or aspects of the disclosure are described in terms of Markush groups, those skilled in the art will recognize that the disclosure is also thereby described in terms of any individual member or subgroup of members of the Markush group.

As will be understood by one skilled in the art, for any and all purposes, particularly in terms of providing a written description, all ranges disclosed herein also encompass any and all possible subranges and combinations of subranges thereof. Any listed range can be easily recognized as sufficiently describing and enabling the same range being broken down into at least equal halves, thirds, quarters, fifths, tenths, etc. As a non-limiting example, each range discussed herein can be readily broken down into a lower third, middle third and upper third, etc. As will also be understood by one skilled in the art, all language such as "up to," "at least," "greater than," "less than," and the like, include the number recited and refer to ranges which can be subsequently broken down into subranges as discussed above. Finally, as will be understood by one skilled in the art, a range includes each individual member.

While certain embodiments have been illustrated and described, it should be understood that changes and modifications can be made therein in accordance with ordinary skill in the art without departing from the technology in its broader aspects as defined in the following claims.

What is claimed is:

1. A method of treating a composition comprising a bisphenol A (BPA) precursor, the method comprising:
    contacting the composition comprising the BPA precursor with a carboxylic acid-reducing composition, wherein the carboxylic acid-reducing composition comprises a carboxylic acid-reducing enzyme and organic silane, and
    wherein the BPA precursor comprises a polymer that produces BPA monomers upon polymer hydrolysis.

2. The method of claim 1, wherein the BPA precursor comprises polycarbonate, polyester carbonate, or an epoxy resin.

3. The method of claim 1, wherein the organic silane is formed from polymerization of methyltrimethoxysilane and gamma-aminopropyltriethoxysilane.

4. The method of claim 1, wherein the carboxylic acid-reducing enzyme is entrapped in the organic silane.

5. The method of claim 1, wherein at least one carboxylic acid-reducing enzyme is selected from carboxylate reductase, aldehyde ferredoxin oxidoreductase, formaldehyde ferredoxin oxidoreductase, glyceraldehyde-3-phosphate ferredoxin oxidoreductase, and (2R)-hydroxycarboxylate-viologen-oxidoreductase.

6. The method of claim 1, wherein the carboxylic acid-reducing composition is in the form of a gel suspended in an adhesive film.

7. The method of claim 1, wherein the carboxylic acid-reducing composition is contacted with at least a portion of the composition comprising the BPA precursor.

8. The method of claim 1, wherein contacting comprises polymerizing the carboxylic acid-reducing composition directly onto at least a portion of the composition comprising the BPA precursor.

9. A method of treating water that contains 2,2-bis(4-hydroxyphenyl)propanoic acid (BPA-COOH), the method comprising:
    contacting the water with (a) at least one carboxylic acid-reducing enzyme entrapped in a polymer, and (b) at least one carbonyl-reducing composition under conditions wherein the BPA-COOH is degraded.

10. The method of claim 9, wherein at least one carboxylic acid-reducing enzyme comprises one or more of carboxylate reductase, aldehyde ferredoxin oxidoreductase, formaldehyde ferredoxin oxidoreductase, glyceraldehyde-3-phosphate ferredoxin oxidoreductase, and (2R)-hydroxycarboxylate-viologen-oxidoreductase.

11. The method of claim 9, wherein the carbonyl-reducing composition is one or more of sodium borohydride, lithium aminoborohydride, and alcohol dehydrogenase.

12. The method of claim 9, wherein the carboxylic acid-reducing enzyme and the carbonyl-reducing composition are contacted with the water sequentially.

13. The method of claim 9, wherein the polymer is organic silane.

14. The method of claim 13, wherein the organic silane is formed from polymerization of methyltrimethoxysilane and gamma-aminopropyltriethoxysilane.

15. A water treatment system that contains 2,2-bis(4-hydroxyphenyl)propanoic acid (BPA-COOH), comprising:
    (a) an inlet to a treatment area, wherein the treatment area holds (i) a carboxylic acid-reducing composition comprising at least one carboxylic acid-reducing enzyme entrapped in polymerized organic silane, and (ii) at least one carbonyl-reducing composition; and
    (b) an outlet from the treatment area.

16. The water treatment system of claim 15, wherein the organic silane is formed from polymerization of methyltrimethoxysilane and gamma-aminopropyltriethoxysilane.

17. The water treatment system of claim 15, wherein at least one carboxylic acid-reducing enzyme comprises one or more of carboxylate reductase, aldehyde ferredoxin oxidoreductase, formaldehyde ferredoxin oxidoreductase, glyceraldehyde-3-phosphate ferredoxin oxidoreductase, and (2R)-hydroxycarboxylate-viologen-oxidoreductase.

18. The water treatment system of claim 15, wherein the at least one carbonyl-reducing compound is one or more of sodium borohydride, lithium aminoborohydride, and alcohol dehydrogenase.

19. The water treatment system of claim 15, wherein the carboxylic acid-reducing composition is in the form of one or more of a non-perforated sheet, a perforated sheet, or beads.

20. The water treatment system of claim 15, wherein the treatment area further comprises a first chamber that holds the carboxylic acid-reducing composition and a second chamber that holds the carbonyl-reducing composition.

* * * * *

UNITED STATES PATENT AND TRADEMARK OFFICE
CERTIFICATE OF CORRECTION

PATENT NO. : 9,133,045 B2  
APPLICATION NO. : 13/978239  
DATED : September 15, 2015  
INVENTOR(S) : Xu et al.

Page 1 of 1

It is certified that error appears in the above-identified patent and that said Letters Patent is hereby corrected as shown below:

In the specification

In Column 1, Line 9, delete "§371" and insert -- § 371 --, therefor.

Signed and Sealed this
Twenty-sixth Day of April, 2016

Michelle K. Lee
*Director of the United States Patent and Trademark Office*